US010322093B2

(12) United States Patent
Mueller et al.

(10) Patent No.: US 10,322,093 B2
(45) Date of Patent: Jun. 18, 2019

(54) METHOD FOR PRODUCING A TRANSDERMAL THERAPEUTIC SYSTEM WHICH CONTAINS A D2 AGONIST

(75) Inventors: Walter Mueller, Neuwied (DE); James V. Peck, Richmond, VA (US)

(73) Assignees: UCB BIOPHARMA SPRL, Brussels (BE); LTS LOHMANN THERAPIE-SYSTEME AG, Andernach (DE)

( * ) Notice: Subject to any disclaimer, the term of this patent is extended or adjusted under 35 U.S.C. 154(b) by 1284 days.

(21) Appl. No.: 10/936,620

(22) Filed: Sep. 7, 2004

(65) Prior Publication Data

US 2005/0033065 A1  Feb. 10, 2005

Related U.S. Application Data

(62) Division of application No. 09/647,290, filed as application No. PCT/EP99/01795 on Mar. 18, 1999, now Pat. No. 6,884,434.

(30) Foreign Application Priority Data

Mar. 30, 1998 (DE) .................. 198 14 084

(51) Int. Cl.
*A61K 9/70* (2006.01)
*A61K 31/381* (2006.01)
(52) U.S. Cl.
CPC .......... *A61K 9/7061* (2013.01); *A61K 9/703* (2013.01); *A61K 9/7023* (2013.01);
(Continued)

(58) Field of Classification Search
CPC .. A61K 31/381; A61K 9/7069; A61K 9/7061; A61K 9/7084; A61K 9/703; A61K 9/7092; A61K 9/7023; A61K 9/7038
See application file for complete search history.

(56) References Cited

U.S. PATENT DOCUMENTS 4,863,970 A  9/1989  Patel et al. .................. 514/772
4,915,950 A  4/1990  Miranda et al. ............. 424/448
(Continued)

FOREIGN PATENT DOCUMENTS

CA  2 532 804  2/2005
CA  2 532 859  2/2005
(Continued)

OTHER PUBLICATIONS

"Transdermal administration of the dopamine agonist N-0437 and seven ester prodrugs: comparison with oral administration in the 6-OHDA turning model", Izaak et al. Pharmacology (1990) 342:655-659.*

(Continued)

*Primary Examiner* — Isis A Ghali
(74) *Attorney, Agent, or Firm* — Harness, Dickey and Pierce, P.L.C.

(57) ABSTRACT

A substantially solvent-free matrix layer containing (−)-5,6,7,8-tetrahydro-6-[propyl-[2-(2-thienyl)ethyl]amino]-1-naphthalenol is produced by adding an active substance to an adhesive solution, coating the resultant active substance-containing adhesive solution onto a suitable sheet, and removing the solvents in a drying process to give said substantially solvent-free matrix layer.

19 Claims, 1 Drawing Sheet

(52) U.S. Cl.
CPC .......... *A61K 9/7038* (2013.01); *A61K 9/7069* (2013.01); *A61K 9/7084* (2013.01); *A61K 9/7092* (2013.01); *A61K 31/381* (2013.01)

(56) References Cited

U.S. PATENT DOCUMENTS

| | | | |
|---|---|---|---|
| 4,942,037 A | 7/1990 | Bondi et al. | 424/448 |
| 4,973,468 A | 11/1990 | Chiang et al. | 424/449 |
| 5,043,482 A * | 8/1991 | Maignan et al. | 568/734 |
| 5,069,909 A | 12/1991 | Sharma et al. | 424/449 |
| 5,091,186 A | 2/1992 | Miranda et al. | 424/448 |
| 5,124,157 A | 6/1992 | Colley et al. | 424/448 |
| 5,147,916 A | 9/1992 | Sweet | 524/266 |
| 5,177,112 A | 1/1993 | Horn | 514/65 |
| 5,225,198 A | 7/1993 | Sharma et al. | 424/443 |
| 5,234,690 A | 8/1993 | Chiang et al. | 424/448 |
| 5,246,997 A | 9/1993 | Sweet | 524/266 |
| 5,252,334 A | 10/1993 | Chiang et al. | 424/448 |
| 5,252,335 A | 10/1993 | Chiang | 424/449 |
| 5,268,385 A | 12/1993 | Horn | |
| 5,271,940 A | 12/1993 | Cleary et al. | 424/448 |
| 5,273,755 A | 12/1993 | Venkatraman et al. | 424/448 |
| 5,273,756 A | 12/1993 | Fallon et al. | 424/448 |
| 5,273,757 A | 12/1993 | Jaeger et al. | 424/448 |
| 5,308,625 A | 5/1994 | Wong et al. | 424/449 |
| 5,382,569 A * | 1/1995 | Cody et al. | 514/17 |
| 5,382,596 A | 1/1995 | Sleevi et al. | 514/459 |
| 5,393,529 A | 2/1995 | Hoffman et al. | 424/449 |
| 5,456,745 A | 10/1995 | Roreger et al. | 106/128 |
| 5,462,746 A * | 10/1995 | Wolter et al. | 424/449 |
| 5,554,381 A | 9/1996 | Roos et al. | 424/449 |
| 5,601,839 A | 2/1997 | Quan et al. | 424/448 |
| 5,656,286 A | 8/1997 | Miranda et al. | |
| 5,670,164 A | 9/1997 | Meconi et al. | 424/448 |
| 5,688,524 A | 11/1997 | Hsu et al. | 424/449 |
| 5,733,571 A | 3/1998 | Sackler | 424/449 |
| 5,771,890 A | 6/1998 | Tamada | 128/635 |
| 5,807,570 A | 9/1998 | Chen et al. | 424/449 |
| 5,817,332 A | 10/1998 | Urtti et al. | 424/449 |
| 5,830,497 A * | 11/1998 | Yamanaka et al. | 424/448 |
| 5,834,010 A | 11/1998 | Quan et al. | 424/448 |
| 5,840,336 A | 11/1998 | Hsu et al. | 424/484 |
| 5,843,472 A | 12/1998 | Ma et al. | 424/449 |
| 5,876,746 A | 3/1999 | Jona et al. | 424/449 |
| 5,879,701 A | 3/1999 | Aduett et al. | 424/448 |
| 5,891,461 A | 4/1999 | Jona et al. | 424/449 |
| 5,902,603 A | 5/1999 | Chen et al. | 424/449 |
| 5,906,830 A | 5/1999 | Farinas et al. | 424/448 |
| 5,980,932 A | 11/1999 | Chiang et al. | |
| 6,024,974 A | 2/2000 | Li | 424/448 |
| 6,024,976 A | 2/2000 | Miranda et al. | 424/448 |
| 6,063,398 A | 5/2000 | Gueret | 424/443 |
| 6,218,421 B1 | 4/2001 | King | 514/421 |
| 6,316,022 B1 | 11/2001 | Mantelle et al. | 424/448 |
| 6,393,318 B1 | 5/2002 | Conn et al. | 604/20 |
| 6,398,562 B1 | 6/2002 | Butler et al. | 439/91 |
| 6,372,920 B1 | 8/2002 | Minaskanian et al. | 549/75 |
| 6,465,004 B1 | 10/2002 | Rossi-Montero et al. | 424/448 |
| 6,620,429 B1 | 9/2003 | Müller | 424/449 |
| 6,685,959 B1 | 2/2004 | Moreau et al. | 424/449 |
| 6,687,522 B2 | 2/2004 | Tamada | 600/347 |
| 6,699,498 B1 | 3/2004 | Müller | 424/449 |
| 6,884,434 B1 | 4/2005 | Mueller et al. | 424/487 |
| 6,899,894 B1 | 5/2005 | Klein et al. | 424/448 |
| 7,309,497 B2 | 12/2007 | Rimpler et al. | 424/422 |
| 7,413,747 B2 | 8/2008 | Mueller et al. | 424/448 |
| 8,545,872 B2 | 10/2013 | Breitenbach | |
| 8,592,477 B2 | 11/2013 | Wolff et al. | |
| 8,617,591 B2 | 12/2013 | Schacht et al. | |
| 8,754,120 B2 | 6/2014 | Bouwstra et al. | |
| 2002/0110585 A1 | 8/2002 | Godbey et al. | 424/449 |
| 2003/0026830 A1 | 2/2003 | Lautertback et al. | 424/449 |
| 2003/0027793 A1 | 2/2003 | Lautertback et al. | 514/63 |
| 2003/0166709 A1 | 9/2003 | Rimpler et al. | 514/447 |
| 2004/0034083 A1 | 2/2004 | Stephenson et al. | 514/406 |
| 2004/0048779 A1 | 3/2004 | Schollmayer | 514/2 |
| 2004/0057985 A1 | 3/2004 | Bracht | |
| 2004/0081683 A1 | 4/2004 | Schacht et al. | 424/449 |
| 2004/0110673 A1 | 6/2004 | Steinkasserer et al. | 514/12 |
| 2004/0116537 A1 | 6/2004 | Li et al. | 514/663 |
| 2004/0137045 A1 | 7/2004 | Breitenbach et al. | 424/449 |
| 2004/0209861 A1 | 10/2004 | Benavides et al. | 514/210.01 |
| 2005/0079206 A1 | 4/2005 | Schacht et al. | 424/449 |
| 2005/0136101 A1 | 6/2005 | Berthold | 424/448 |
| 2005/0175678 A1 | 8/2005 | Breitenbach | 424/448 |
| 2005/0175680 A1 | 8/2005 | Breitenbach | 424/448 |
| 2005/0197385 A1 | 9/2005 | Scheller et al. | 514/438 |
| 2005/0260254 A1 | 11/2005 | Breitenbach et al. | 424/449 |
| 2006/0216336 A1 | 9/2006 | Wolff | |
| 2006/0222691 A1 | 10/2006 | Cantor et al. | 424/448 |
| 2006/0263419 A1 | 11/2006 | Wolff | 424/448 |
| 2007/0072917 A1 | 3/2007 | Scheller et al. | 514/357 |
| 2007/0093546 A1 | 4/2007 | Scheller et al. | 514/447 |
| 2007/0191308 A1 | 8/2007 | Kramer | 514/60 |
| 2007/0191470 A1 | 8/2007 | Scheller | 514/438 |
| 2007/0197480 A1 | 8/2007 | Scheller et al. | 514/114 |
| 2008/0008748 A1 | 1/2008 | Beyreuther et al. | 424/449 |
| 2008/0138389 A1 | 6/2008 | Muller et al. | 424/448 |
| 2008/0146622 A1 | 6/2008 | Scheller et al. | 514/357 |
| 2008/0274061 A1 | 11/2008 | Schollmayer et al. | 424/45 |
| 2009/0143460 A1 | 6/2009 | Wolff et al. | 514/438 |
| 2011/0104281 A1 | 5/2011 | Beyreuther et al. | |
| 2012/0322845 A1 | 12/2012 | Wolff et al. | |
| 2013/0251791 A1 | 9/2013 | Seth et al. | |
| 2014/0051768 A1 | 2/2014 | Scheller et al. | |
| 2014/0243386 A1 | 8/2014 | Bouwstra et al. | |

FOREIGN PATENT DOCUMENTS

| | | |
|---|---|---|
| CA | 2 547 820 | 6/2005 |
| CA | 2 546 797 | 7/2005 |
| EP | 0 180 377 | 1/1991 |
| EP | 524776 A1 * | 1/1993 |
| EP | 0 524 776 | 8/1995 |
| WO | WO 93/07842 | 4/1993 |
| WO | WO 93/14727 | 8/1993 |
| WO | WO 93/16073 | 8/1993 |
| WO | WO 94/04109 | 3/1994 |
| WO | WO 94/07468 | 4/1994 |
| WO | WO 9407468 A1 * | 4/1994 |
| WO | WO 95/00122 | 1/1995 |
| WO | WO 95/01767 | 1/1995 |
| WO | WO 95/05137 | 2/1995 |
| WO | WO 95/05138 | 2/1995 |
| WO | WO 9518603 A1 * | 7/1995 |
| WO | WO 95/24776 | 9/1995 |
| WO | WO 96/00110 | 1/1996 |
| WO | WO 96/22083 | 7/1996 |
| WO | WO 96/22084 | 7/1996 |
| WO | WO 96/39136 | 12/1996 |
| WO | WO 96/40087 | 12/1996 |
| WO | WO 97/09971 | 3/1997 |
| WO | WO 97/11696 | 4/1997 |
| WO | WO 97/29735 | 8/1997 |

OTHER PUBLICATIONS

"The influence of azone on the transdermal penetration of the dopamine D2 agonist N-0923 in freely moving rats" Swart et al., International Journal of Pharmaceutics, 88 (1992) 165-170.*
"Two-Phase Matrix for the Delivery of N-0923, A dopamine agonist", Chiang et al., Proceed. Interm. Symp. Control. Rel. Bioact. Mater., 22 (1995), Controlled Release Society, Inc.*
"The determination of the pH of the skin of man and common laboratory animals", Draize, J Invent. Dermatol. 5:77-85, 1942.*
Blindauer (2003) Arch. Neurol. 60(12): 1721-1728.
Chiang et al. (1995) Proc. Int. Symp. Controlled Release Bioact Mater. $22^{nd}$, 710-711.
Den Daas et al. (1990) Naunyn-Schmiedeger's Pharmacol. 342, 655-659.
Hsu et al. (1992) Cygnus Therapeutic Systems Project Report N-0923, 2-19.

(56) References Cited

OTHER PUBLICATIONS

Levien et al. (2005) Advances in Pharmacy 3(1): 62-92.
LeWitt et al. (2007) Neurology 68: 1262-1267.
Loschman et al. (1989) Eur. J. Pharmacol. 373-380.
Pfister (1988) Drug and Cosmetic Ind. (Oct): 44-52.
Pfister (1989) Pharm. Tech. (March): 126-138.
Pfister and Hsieh (1990) Pharm. Tech. (Sept): 132-140.
Pfister and Hsieh (1990) Pharm. Tech. (Oct): 54-60.
Pfister et al. (1991) Chemistry in Britain (Jan): 43-46.
Pfister et al. (1992) Pharm. Tech. (Jan): 42-58 and 83.
Roy et al. (1996) J. Pharn. Science 85(5): 491-495.
Swart et al. (1992) Int. J. Pharm. 88(1-3), 165-170.
Thomas et al. (1991) STP Pharma Sci 1(1): 38-46.
Timmerman et aL (1989) Eur. J. Pharmacol. 162: 143-150.
Walters et al. (1995) J. Chromatogr. B. Biomed Appl. 299-307.
Office Action, dated Jun. 9, 2010 issued in U.S. Appl. No. 11/931,762.
Office Action, dated Apr. 27, 2010 issued in U.S. Appl. No. 10/627,990.
Office Action, dated Aug. 3, 2010 issued in U.S. Appl. No. 10/517,157.
Office Action, dated Jun. 7, 2010 issued in U.S. Appl. No. 10/587,637.
Office Action, dated May 27, 2010 issued in U.S. Appl. No. 10/565,699.
Office Action, dated Apr. 15, 2002 issued in U.S. Appl. No. 09/647,290.
Office Action, dated Nov. 1, 2002 issued in U.S. Appl. No. 09/647,290.
Office Action, dated Aug. 17, 2007 issued in U.S. Appl. No. 10/623,864.
Office Action, dated Aug. 18, 2009 issued in U.S. Appl. No. 10/627,990.
Office Action, dated Feb. 2, 2009 issued in U.S. Appl. No. 10/627,990.
Office Action, dated Dec. 23, 2009 issued in U.S. Appl. No. 10/429,283.
Office Action, dated Jan. 8, 2008 issued in U.S. Appl. No. 10/429,283.
Office Action, dated Mar. 30, 2009 issued in U.S. Appl. No. 10/429,283.
Office Action, dated Sep. 12, 2008 issued in U.S. Appl. No. 10/429,283.
Office Action, dated Sep. 21, 2006 issued in U.S. Appl. No. 10/429,283.
Office Action, dated Feb. 19, 2009 issued in U.S. Appl. No. 10/713,424.
Office Action, dated Jun. 25, 2008 issued in U.S. Appl. No. 10/713,424.
Office Action, dated Mar. 23, 2007 issued in U.S. Appl. No. 10/713,424.
Office Action, dated Sep. 14, 2007 issued in U.S. Appl. No. 10/713,424.
Office Action, dated Jan. 23, 2008 issued in U.S. Appl. No. 11/931,666.
Office Action, dated Oct. 16, 2008 issued in U.S. Appl. No. 10/587,637.
Office Action, dated Sep. 2, 2009 issued in U.S. Appl. No. 10/587,637.
Office Action, dated Mar. 6, 2009 issued in U.S. Appl. No. 10/517,157.
Office Action, dated Oct. 15, 2009 issued in U.S. Appl. No. 10/139,894.
Office Action, dated Oct. 23, 2009 issued in U.S. Appl. No. 10/565,699.
Van der Weide, et al. (1988) "The enantiomers of the D-2 dopamine receptor agonist N-0437 discriminate between pre- and postsynaptic dopamine receptors." Eur J Pharmacol 146:319-326.
Makeni Chemical Technical Data, "Kollidon 90", Aug. 31, 2004.
Office Action dated Oct. 1, 2010 issued in U.S. Appl. No. 10/429,283.
Office Action dated Dec. 2, 2011 issued in U.S. Appl. No. 10/140,096.
Office Action dated Feb. 3, 2012 issued in U.S. Appl. No. 10/429,283.
Office Action dated May 3, 2013 issued in U.S. Appl. No. 10/429,283.
Office Action dated May 4, 2011 issued in U.S. Appl. No. 10/429,283.
Office Action dated Dec. 7, 2011 issued in U.S. Appl. No. 11/931,762.
Office Action dated Feb. 7, 2008 issued in U.S. Appl. No. 10/523,908.
Office Action dated Feb. 8, 2011 issued in U.S. Appl. No. 11/931,762.
Office Action dated Nov. 8, 2011 issued in U.S. Appl. No. 10/565,699.
Office Action dated Feb. 10, 2009 issued in U.S. Appl. No. 10/139,894.
Office Action dated Sep. 10, 2008 issued in U.S. Appl. No. 10/429,283.
Office Action dated Jun. 11, 2012 issued in U.S. Appl. No. 12/744,989.
Office Action dated Feb. 12, 2009 issued in U.S. Appl. No. 10/140,096.
Office Action dated Jul. 12, 2012 issued in U.S. Appl. No. 13/457,848.
Office Action dated May 12, 2011 issued in U.S. Appl. No. 10/623,864.
Office Action dated May 12, 2011 issued in U.S. Appl. No. 11/239,701.
Office Action dated Feb. 14, 2011 issued in U.S. Appl. No. 10/565,699.
Office Action dated Aug. 15, 2012 issued in U.S. Appl. No. 13/020,414.
Office Action dated Jan. 15, 2014 issued in U.S. Appl. No. 10/429,283.
Office Action dated Aug. 16, 2010 issued in U.S. Appl. No. 11/239,701.
Office Action dated Dec. 17, 2009 issued in U.S. Appl. No. 10/140,096.
Office Action dated Dec. 18, 2012 issued in U.S. Appl. No. 10/140,096.
Office Action dated Oct. 18, 2011 issued in U.S. Appl. No. 11/239,701.
Office Action dated Dec. 19, 2012 issued in U.S. Appl. No. 10/139,894.
Office Action dated Oct. 19, 2011 issued in U.S. Appl. No. 10/139,894.
Office Action dated Dec. 21, 2009 issued in U.S. Appl. No. 11/239,701.
Office Action dated Apr. 24, 2013 issued in U.S. Appl. No. 10/565,699.
Office Action dated Jun. 24, 2009 issued in U.S. Appl. No. 11/931,762.
Office Action dated May 24, 2011 issued in U.S. Appl. No. 10/140,096.
Office Action dated Jul. 27, 2015 issued in U.S. Appl. No. 11/931,762.
Office Action dated Oct. 31, 2011 issued in U.S. Appl. No. 10/627,990.
Swart, P.J. et al., "In Vitro Penetration of the Dopamine D2 agonist N-0923 With and Without Azone", *International Journal of Pharmaceutics* (1992), 87:67-72.

\* cited by examiner

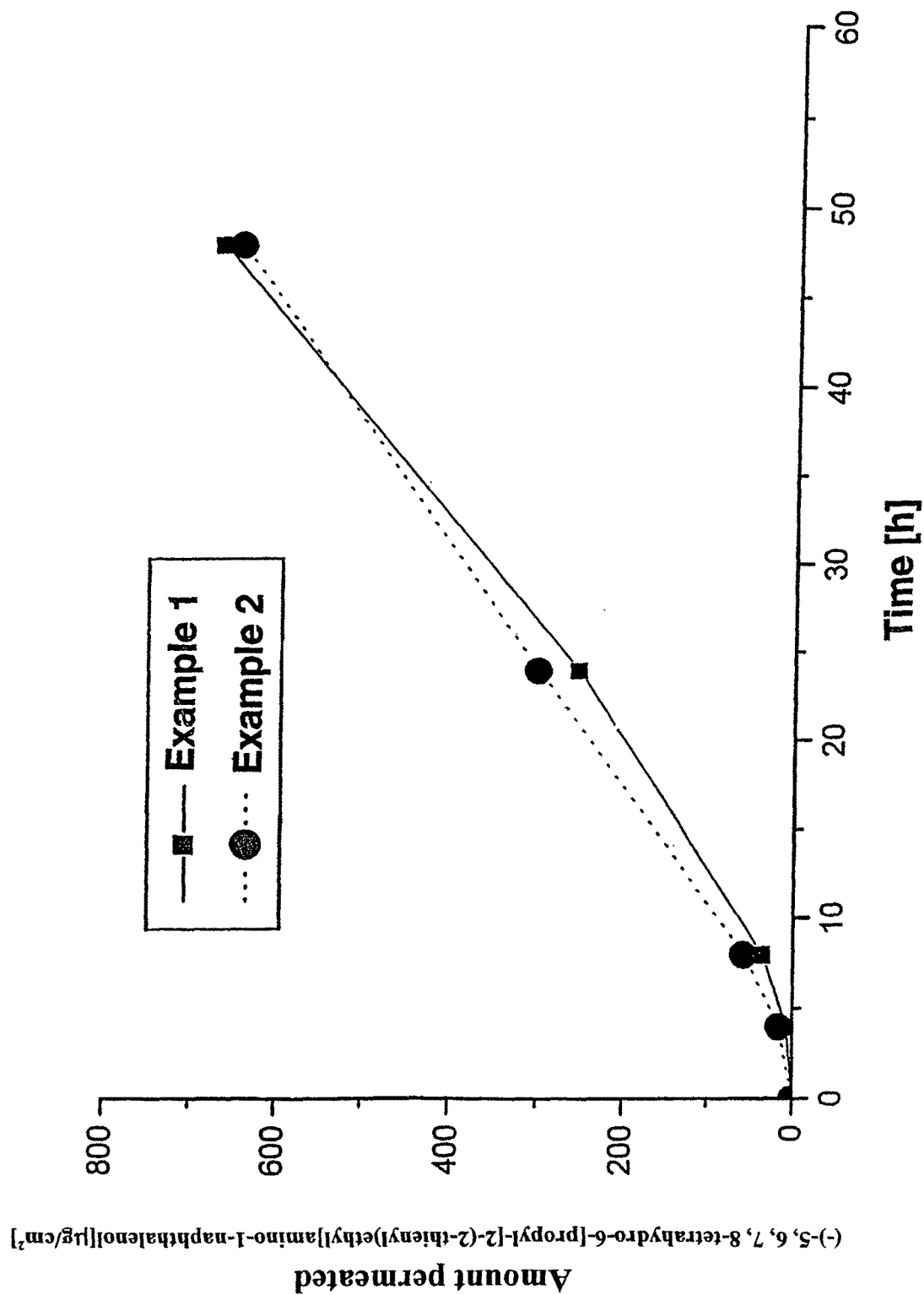

METHOD FOR PRODUCING A TRANSDERMAL THERAPEUTIC SYSTEM WHICH CONTAINS A D2 AGONIST

REFERENCE TO RELATED APPLICATION

This is a divisional application of application Ser. No. 09/647,290, filed Nov. 28, 2000, representing national entry under 35 U.S.C. § 371 of international patent application No. PCT/EP99/01795, filed Mar. 18, 1999, which claims priority under 35 U.S.C. 119 of German Application No. DE 198 14 084, filed Mar. 30, 1998, the full disclosure of each of which is incorporated herein by reference.

BACKGROUND OF THE INVENTION

The invention relates to a transdermal therapeutic system for the treatment of Parkinson's syndrome, comprising a backing layer which is inert to the ingredients of the matrix, a self-adhesive matrix layer containing (−)-5,6,7,8-tetrahydro-6-[propyl-[2-(2-thienyl)ethyl]amino]-1-naphthalenol having the below-indicated formula

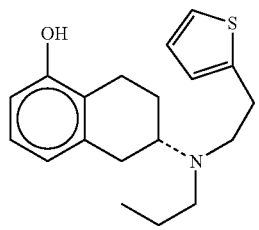

in an effective amount, and a protective layer which is to be removed prior to use.

Worldwide about 2.5-3% of the population suffer from so-called Parkinson's syndrome, which breaks out mainly at the age between 58 and 62. The symptoms of this disease manifest themselves in motorial disorders such as trembling, muscle stiffening, vegetative disorders such as increased flow of saliva and tears, disturbed thermoregulation, hypopiesia and functional disorders of bladder and intestine, as well as psychic disorders such as irresoluteness and depressive mood.

Parkinson's syndrome is caused by the degeneration of dopaminergic neurons in the substantia nigra. This leads to the depletion of dopamine in certain cerebral regions, in particular in the brain stem ganglia. The resultant disturbed balance between the neurotransmitters acetylcholine and dopamine is in the end responsible for the symptoms of the disease. A predominance of acetylcholine is responsible for the so-called plus symptoms, and a deficiency of dopamine is responsible for the so-called minus symptoms.

Parkinson's syndrome can therefore be treated with so-called anticholinergics or levodopa. Anticholinergics impede the cholinergic neurotransmission, and levodopa passes, as precursor of dopamine, the blood-brain barrier and is converted in the brain to dopamine.

Another path of treatment of Parkinson's syndrome is the treatment with dopamine receptor agonists. Dopamine agonists are substances which, although structurally different from dopamine, bind to the same receptors and trigger an effect similar to that of dopamine. Due to their molecular structure dopamine receptor agonists have properties which enable them to overcome the blood-brain barrier. In this connection it is advantageous if the substances bind selectively to a subgroup of the dopamine receptors, the D2-receptors, as this decreases side effects. In this connection, the substance (−)-5,6,7,8 tetrahydro-6-[propyl-[2-(2-thienyl)ethyl]amino]-1-naphthalenol having the above-indicated formula, has proved an especially effective selective D2-agonist.

Due to this compound's half-life and high first-pass effect, oral administration of this substance is, however, very problematic. The short half-life would necessitate frequent intake of the substance, and the high first-pass effect would necessitate high dosage. Whereas the intake frequency may possibly be overcome by an appropriate oral formulation, the problem of high first-pass effect can be solved in principal only by a non-oral administration of the active substance.

A transdermal system designed for the administration of a D2-agonist of the above-indicated formula has already been described in WO 94-07468. This system contains the active substance as hydrochloride in a two-phase matrix which is formed substantially by a hydrophobe polymer material, which is present as a continuous phase, with hydrated silicate dispersed therein for taking up the hydrophile drug salt, and additionally contains, or may contain, hydrophobic solvents, permeation-enhancing agents and dispersing agents.

This system has the disadvantage that the active substance salt must be mixed with the silicate in aqueous solution, and that an additional emulsifier is necessary to emulsify this aqueous solution with the lipophile polymer, which is dissolved in an organic solvent—commonly hexane, heptane or ethyl acetate. Due to coating problems, it is much more difficult to manufacture transdermal systems using this emulsion. In addition, for such systems only the salt can be used, since only the salt is sufficiently hydrophile to be soluble in water.

It is thus the object of the invention to develop systems for (−)-5,6,7,8-tetrahydro-6-[propyl-[2-(2-thienyl)ethyl]amino]-1-naphthalenol avoiding the disadvantages of the system described in WO 94-07468.

In this connection, the invention particularly focuses on optimizing active substance uptake within the system, and skin transfer.

SUMMARY OF THE INVENTION

The transdermal therapeutic system according to this invention, of the kind mentioned at the beginning and developed in accordance with the above, is essentially characterized by a matrix on the basis of an acrylate-based or silicone-based non-aqueous polymer adhesive system having a solubility for the free D2-agonist base (−)-5,6,7,8-tetrahydro-6-[propyl-[2-(2-thienyl)ethyl]amino]-1-naphthalenol of >5% (w/w), which matrix is substantially free of inorganic silicate particulates. The solubility is determined at ambient temperature.

BRIEF DESCRIPTION OF THE DRAWINGS

The drawing is a plot of amount of (−)-5,6,7,8-tetrahydro-6-[propyl-[2-(2-thienyl)ethyl]amino]-1-naphthalenol permeated versus time.

DETAILED DESCRIPTION OF THE INVENTION

In their simplest embodiment, the matrix systems are single-phase matrices. They consist of a backing layer, an active substance-containing self-adhesive matrix, and a protective film to be removed prior to use. More complicated embodiments contain multiple-layer matrices that may also contain non-adhesive layers and control membranes.

Polyacrylates are produced by radical polymerization of acrylic acid derivatives or methacrylic acid derivatives, it being quite possible to also use other suitable compounds such as, for example, vinyl acetate, as additional monomers. By selecting corresponding monomers it is possible to give each resultant adhesive specific properties.

It is common to crosslink polyacrylates with multivalent metal ions to enhance the physical properties of the adhesive or adapt it to the given requirements. Said metal ions are mostly used in the form of metal chelates which are soluble in organic solvents. Suitable compounds are, in particular, aluminum acetylacetonate or titanium acetylacetonate.

Silicone adhesives are in most cases polydimethylsiloxanes. However, other organic residues such as, for example, ethyl groups or phenyl groups may in principle be present instead of the methyl groups. Such silicone adhesives are available as one-component adhesives in two variants, as so-called amine-resistant and as non-amine-resistant adhesives. Due to the basic nature of (−)-5,6,7,8-tetrahydro-6-[propyl-[2-(2-thienyl)ethyl]amino]-1-naphthalenol, for a silicone adhesive containing this active substance, amine-resistant adhesives are used.

Such amine-resistant silicone adhesives stand out for their not having free silanol functions. In a special process the Si—OH groups are provided with an alkyl residue. Such adhesives and their production are described in detail in EP 0 180 377.

The adhesive's dissolving capacity for the active substance is an important parameter for the development of matrix systems, just as the mobility of the active substance in the matrix, and its transfer via the contact surface to the skin, which transfer is substantially determined by corresponding distribution coefficients and the skin absorption. This results in a relatively complicated set of influences which have to be taken into account.

In systems wherein the active substance is only partially dissolved the concentration of the dissolved active substance is equal to the saturation concentration and thus has the maximum thermodynamic activity under these conditions. In general, it is, above all, the kind and quantity of the free functional groups in the adhesive which are important for the dissolving capacity of the polyacrylate adhesives. With respect to (−)-5,6,7,8-tetrahydro-6-[propyl-[2-(2-thienyl)ethyl]amino]-1-naphthalenol, however, it was found that the solubility of the free base is largely independent thereof, and lies in the range of between 15-35% (w/w). Such a system must therefore contain the active substance in a concentration of at least 10% (w/w) in order to come sufficiently near to the maximal thermodynamic activity. For the hydrochloride of (−)-5,6,7,8-tetrahydro-6-[propyl-[2-(2-thienyl)ethyl] amino]-1-naphthalenol the solubility in polyacrylates having 5-10% (w/w) is much lower, so that in such systems the active substance is preferably only partially dissolved.

Since, due to its hydrophilic properties, the hydrochloride can pass the barrier of the stratum corneum only poorly, it is necessary in this case to use lipophile, monovalent acids such as, for example, oleic acid, which, in the patch matrix, partially converts the hydrochloride into the more lipophilic oleate and which, moreover, generally acts as a permeation enhancer in the skin.

Advantageously, the acrylate-based polymer adhesive contains at least two of the following monomers: acrylic acid, acrylamide, hexylacrylate, 2-ethylhexylacrylate, hydroxyethylacrylate, octylacrylate, butylacrylate, methylacrylate, glycidylacrylate, methacrylic acid, methacrylamide, hexylmethacrylate, 2-ethylhexylmethacrylate, octylmethacrylate, methylmethacrylate, glycidylmethacrylate, vinylacetate or vinylpyrrolidone.

Silicone adhesives have a comparatively low dissolving capacity for most active substances. The saturation capacity for the base (−)-5,6,7,8-tetrahydro-6-(propyl-[2-(2-thienyl) ethyl]amino]-1-naphthalenol and the hydrochloride, respectively, is about 5% (w/w), whereas the corresponding salts are practically insoluble therein. Thus, in connection with silicone adhesives only the active substance base is suitable. If a suitable substance having an increased solubility for the active substance is admixed to the silicone adhesive, the dissolving capacity for the free base in such matrices can be raised to up to 40% (w/w) without adversely affecting the physical properties of the matrix. Suitable substances are, for example, soluble polyvinylpyrrolidone, copolymers of vinylpyrrolidone and vinylacetate, polyethyleneglycol, polypropylene glycol, glycerol or fatty acid esters of glycerol, or copolymers of ethylene and vinylacetate, polyvinylpyrrolidone having proved particularly suitable.

About 1.5-5% (w/w) of polyvinylpyrrolidone in an amine-resistant silicone adhesive increase the solubility of (−)-5,6,7,8-tetrahydro-6-[propyl-[2-(2-thienyl)ethyl] amino]-1naphthalenol to about 10-15% (w/w). This is sufficient to dissolve 10 mg active substance in a 20 cm$^2$ large patch having a coat weight of the matrix of 50 g/m$^2$. Since with transdermal patch systems one must always assume that only about 50% of the active substance employed will be available during the period of application, given a daily dose in the range of 1-10 mg of the active substance a plaster size of between 2 and 40 cm$^2$ can be expected to be sufficient to achieve therapeutic plasma levels.

The polyvinylpyrrolidone dispersed in the silicone adhesive additionally has the advantage that it decreases the so-called cold flow known from silicone adhesives. The term cold flow in this connection means that the matrix behaves like a strongly viscous fluid and thus, through flowing, tends to take up a larger area. This results in the matrix after a certain time taking up a surface which is larger than the backing layer of the patch, and in the patch tending to become agglutinated to the primary packaging material. This advantage of polyvinylpyrrolidone has already been mentioned in EP 0 524 776.

To produce the patches according to this invention, (−)-5,6,7,8-tetrahydro-6-[propyl-[2-(2-thienyl)ethyl]amino]-1-naphthalenol or the hydrochloride is dissolved or suspended in ethanol or in another suitable organic solvent, and is then added to the adhesive solution while stirring. Where the adhesive has a suitable solvent system, the active substance can also be added to the adhesive solution directly. Additional auxiliary substances can be added either to the adhesive solution, the active substance solution or to the active substance-containing adhesive solution. An auxiliary substance which advantageously is added to the active substance solution directly is, for example, an alkaline substance which is suitable of converting the active substance hydrochloride into the free active substance base. More particularly, it is preferred to use alkali metal hydroxide such as sodium or potassium hydroxide, or an alkali metal silicate such as sodium or potassium trisilicate or sodium or potassium metasilicate as the alkaline substance. After the reaction, the solution may optionally be filtered, whereby the reactants, with the exception of the active substance base, are quantitatively practically eliminated. Said reactants are sodium chloride or potassium chloride in the case that sodium hydroxide or potassium hydroxide, respectively, are used, and sodium chloride or potassium chloride and polymeric silicon dioxide in the case that sodium or potassium silicates, respectively, are used. The resultant active substance containing adhesive solution is coated onto a suitable sheet, and the solvents are removed in a drying process. Thereafter, the backing layer of the patch is laminated onto the substantially solvent-free matrix layer, and the patches are punched out of the total laminate.

The permeation properties are advantageously enhanced by permeation enhancers which may be selected from the group of fatty alcohols, fatty acids, fatty acid esters, fatty acid amides, glycerol or its fatty acid esters, N-methylpyrrolidone, terpenes such as limonene, α-pinene, α-terpineol, carvone, carveol, limonene oxide, pinene oxide, 1,8-eucalyptol.

Details of the production and the permeation rates achieved by the finished patches will be given in the examples and the permeation studies. The polyacrylate adhesives mentioned in Examples 1-3 are to be understood as examples and may be readily replaced by other acrylate adhesives suitable for medicinal use.

The finished plasters were used in permeation studies utilizing Franz diffusion cells and human epidermis. The results are listed in FIGS. 1-3. It will be seen that all plasters are capable of systemically providing a sufficient amount of active substance through the skin. The present invention demonstrates that in the case of the free bases the active substance release is markedly improved as compared to the use of salts. It will also be seen that the silicone adhesive-based plasters, although having a considerably lower active substance content, deliver approximately the same quantity of active substance via the skin as the systems based on polyacrylate adhesives.

Thus, the systems according to the invention make it possible to administer the necessary daily dose of the dopamine agonist of the structure as indicated above transdermally through the skin by means of a patch having a size of approximately 20 cm$^2$ Since the patches can be easily manufactured, and since they deliver the active substance to the skin on their entire matrix surface, and are suitable both for the active substance salts and for the active substance bases, they constitute a considerable improvement over the known systems as described in WO 94/07468.

Example 1: Polyacrylate System with (−)-5,6,7,8-tetrahydro-6-[propyl-[2-(2-thienyl)ethyl]amino]-1-naphthalenol 66 g of a 50% solution of EUDAGRIT® E100 in ethyl acetate are added to 264 g of a solution of a polyacrylate adhesive having a solids content of 50%; after addition of 36 g oleyl alcohol, the mass is homogenized by stirring.

Thereafter, 89.65 g (−)-5,6,7,8-tetrahydro-6-[propyl-[2-(2-thienyl)ethyl]amino]-1-naphthalenol are dissolved in 200 ml methylethylketone and added to the above-mentioned mass while stirring. After homogenization of the mass, it is coated onto a siliconized polyester film using a suitable doctor knife. The thickness of the moist film is adjusted such that after removal of the solvent by drying for 30 minutes at 50° C. a coat weight of 60 g/m$^2$ results.

The dried matrix film is then laminated with a 13 μm-thick polyester film. From the resultant patch laminate, the finished patches are punched out at the desired size, and packed in packaging material bags.

The concentration of (−)-5,6,7,8-tetrahydro-6-[propyl-[2-(2-thienyl)ethyl]amino]-1-naphthalenol base in the patch matrix is 30.8%.

Suitable polyacrylate adhesives are, for example, DURO-TAK® 387-2051, DURO-TAK® 387-2287, DURO-TAK® 387-2353, DURO-TAK® 387-2516, all of National Starch & Chemical.

The permeation rates through human epidermis under in-vitro conditions are shown in FIG. 1.

Example 2: Silicone System with (−)-5,6,7,8-tetrahydro-6-[propyl-[2-(2-thienyl)ethyl]amino]-1-naphthalenol 18 g (−)-5,6,7,8-tetrahydro-6-[propyl-[2-(2-thienyl)ethyl]amino]-1-naphthalenol dissolved in 40 g ethanol are added to 24 g of a 25% solution of KOLLIDON® 90F and the mass is homogenized. Subsequently, 251 g of a solution of an amineresistant silicone adhesive having a solids content of 70% are added to this mass, and the mass is homogenized by further stirring.

Subsequently, the mass is coated, using a suitable doctor knife, onto a polyester film (SCOTCHPAK™ 1022) that has been rendered adhesive, at such a thickness that after removal of the solvents by drying for 30 minutes at 50° C. a coat weight of 50 g/m$^2$ results.

The dried matrix film is then laminated with a 13-μm-thick polyester film. From the resultant patch laminate the finished patches are then punched out in the desired size, and packed in material bags.

The concentration of (−)-5,6,7,8-tetrahydro-6-[propyl-[2 (2-thienyl)ethyl]amino]-1-naphthalenol base in the patch matrix is 9%.

Suitable amine-resistant silicone adhesives are, for example, DOW CORNING® BIO-PSA Q7-4301 and DOW CORNING®.

The permeation rates through human epidermis achieved under in-vitro conditions are shown in FIG. 1.

Example 3: Polyacrylate System with the Hydrochloride of (−)-5,6,7,8-tetrahydro-6-[propyl-[2-(2-thienyl)ethyl]amino]-1-naphthalenol 10 g of the hydrochloride are worked into 70 g polyacrylate adhesive (DURO-TAK® 387-2287, solids content 50%, National Starch & Chemical) and subsequently 4 g oleic acid are added. The mass is then coated onto a siliconized polyester film at such a thickness that after the removal of the solvents a coat weight of 60 g/m$^2$ results. The solvents are removed by drying for 15-20 minutes at a temperature between 40 and 80° C. Thereafter, the dried matrix layer is laminated with a 12-30 μm thick polyester film, and the patches are punched out.

Example 4

20 g (−)-5,6,7,8-tetrahydro-6-[propyl-[2(2-thienyl)ethyl]amino]-1-naphthalenol hydrochloride are stirred, together with 8.0 g sodium metasilicate or 9.1 g sodium trisilicate, in 35 ml ethanol for 48 hours, at room temperature. Optionally, the active substance solution is now filtered and 6.0 g polyvinylpyrrolidone (KOLLIDON® F90, Bayer) in the form of a 25% (w/w) solution in ethanol, and 25 g of a 70% solution of an amine-resistant silicone adhesive (DOW CORNING® BIO-PSA Q7-4301) in heptane are added and the mass is subsequently homogenized by mechanical stirring.

For manufacture of the patch matrix, the mass is subsequently coated onto a suitable film which has been rendered adhesive, and the solvents are removed by drying for 20 minutes at 50° C. The coat weight of the dried matrix film is approximately 50 g/m².

The dried matrix film is laminated with a 23-μm-thick polyester film. The individual patches are punched out of the complete laminate. If the active substance solution is filtered, the composition of the finished patch corresponds to that of the patch according to Example 2.

Example 5

25 g (−)-5,6,7,8-tetrahydro-6-[propyl-[2-(2-thienyl)ethyl]amino]-1-naphthatenol hydrochloride are stirred, together with 14.7 g sodium metasilicate or 16.8 g sodium trisilicate, in 40 ml ethanol for 48 at room temperature. Optionally, the active substance solution is now filtered and 90.2 g oleyl alcohol, 63.2 g of a 52% solution of a polyacrylate adhesive (DURO-TAK® 387-2287, National Starch & Chemical) and 22.8 g of a 40% (w/w) solution of EUDAGRIT® E100 (Rohm-Pharma) are added, and the mass is subsequently homogenized by mechanical stirring.

For manufacture of the patch matrix, the mass is subsequently coated onto a suitable film which has been rendered adhesive, and the solution is removed by drying for 20 minutes at 50° C. The coat weight of the dried matrix film is approximately 80 g/m².

The dried matrix film is laminated with a 23-μm-thick polyester film. The individual patches are punched out of the complete laminate.

Example 6

20 g (−)-5,6,7,8-tetrahydro-6-[propyl-[2-(2-thienyl)ethyl]amino]-1-naphthalenol hydrochloride are added to an ethanolic NaOH or KOH solution which contains equimolar quantities of base (2.27 g NaOH, respectively 3.19 g KOH).

Preferably, the solution has a concentration of 1.5 mol/l. The conversion of the active substance salt takes place within minutes, whereby the greatest part of the NaCl formed precipitates and the active substance base dissolves completely. Optionally, a buffer solution is now added to the active substance solution in order to remove possible excess base. Likewise optionally, the active substance solution can be filtered; 6.0 g polyvinylpyrrolidone (KOLLIDON® F90. Bayer) in the form of a 25% solution (w/w) in ethanol and 250 g of a 70% solution of an amine-resistant silicone adhesive (DOW CORNING® BIO-PSA Q7-4301) in heptane are added, and the mass is subsequently homogenized by mechanical stirring.

For manufacture of the patch matrix, the mass is then coated onto a suitable film which has been rendered adhesive, and the solvents are removed by drying for 20 minutes at 50° C. The coat weight of the dried matrix film is approximately 50 g/m².

The dried matrix film is laminated with 23-μm-thick polyester film. The individual patches are punched out of the complete laminate. If the active substance solution is filtered, the composition of the finished patch corresponds to that of the patch according to Example 2.

Example 7

Analogously to Example 6, 25 g (−)-5,6,7,8-tetrahydro-6-[propyl-[2-(2-thienyl)ethyl)amino]-1-naphthalenol hydrocholoride are reacted with 2.84 g NaOH, respectively 3.99 g KOH, in ethanolic solution. As in Example 6, optionally a buffer is added to the active substance solution, respectively the solution is filtered, and subsequently 9.2 g oleyl alcohol, 63.2 g of a 52% solution of a polyacrylate adhesive (DURO-TAK® 387-2287, National Starch & Chemical) and 22.8 g of a 40% (w/w) solution of EUDAGRIT® E100 (Rohm-Pharma) are added, and the mass is then by mechanical stirring.

For manufacturing the patch matrix, the mass is subsequently coated onto a suitable film which has been rendered adhesive, and the solvents are removed by drying for 20 minutes at 50° C. The coat weight of the dried matrix film is approximately 80 g/m².

The dried matrix film is laminated with a 23-μm-thick polyester film; the individual plasters are punched out of the complete laminate.

The invention claimed is:

1. A method for producing a matrix layer suitable for transdermal administration of a therapeutic effective amount of (−)-5,6,7,8-tetrahydro-6-[propyl-[2-(2-thienyl)ethyl]amino]-1-naphthalenol free base, the method comprising:
    (a) mixing a solution comprising (−)-5,6,7,8-tetrahydro-6-[propyl-[2-(2-thienyl)ethyl]amino]-1-naphthalenol free base and organic solvent with soluble polyvinylpyrrolidone and amine-resistant silicone adhesive to form a mass;
    (b) coating the mass onto a sheet; and
    (c) removing solvent in a drying process.

2. The method of claim 1, wherein the (−)-5,6,7,8-tetrahydro-6-[propyl-[2-(2-thienyl)ethyl]amino]-1-naphthalenol free base is prepared by converting (−)-5,6,7,8-tetrahydro-6-[propyl-[2-(2-thienyl)ethyl]amino]-1-naphthalenol hydrochloride into said free base.

3. The method of claim 2, wherein said (−)-5,6,7,8-tetrahydro-6-[propyl-[2-(2-thienyl)ethyl]amino]-1-naphthalenol hydrochloride is dissolved or suspended in said organic solvent.

4. The method of claim 2, wherein an alkaline substance capable of converting said (−)-5,6,7,8-tetrahydro-6-[propyl-[2-(2-thienyl)ethyl]amino]-1-naphthalenol hydrochloride into the free base is added to the organic solvent prior to or following addition thereto of the adhesive and prior to or following addition thereto of the (−)-5,6,7,8-tetrahydro-6-[propyl-[2-(2-thienyl)ethyl]amino]-1-naphthalenol hydrochloride.

5. The method of claim 4, wherein said alkaline substance comprises an alkali metal hydroxide or an alkali metal silicate.

6. The method of claim 4, wherein said alkaline substance comprises at least one member selected from the group consisting of sodium hydroxide, potassium hydroxide, sodium trisilicate, potassium trisilicate, sodium metasilicate and potassium metasilicate.

7. The method of claim 6, wherein following reaction of (−)-5,6,7,8-tetrahydro-6-[propyl-[2-(2-thienyl)ethyl]amino]-1-naphthalenol hydrochloride with the alkaline substance, the resulting adhesive solution containing (−)-5,6,7,8-tetrahydro-6-[propyl-[2-(2-thienyl)ethyl]amino]-1-naphthalenol free base is filtered to remove at least one by-product selected from the group consisting of sodium chloride, potassium chloride and polymeric silicon dioxide.

8. The method of claim 1, further comprising admixing with said solution at least one permeation enhancer selected from the group consisting of fatty alcohols, fatty acids, fatty acid esters, fatty acid amides, glycerol, fatty acid esters of glycerol, N-methyl-pyrrolidone, terpenes, limonene, a-pinene, a-terpineol, carvone, carveol, limonene oxide, pinene oxide and 1,8-eucalyptol.

9. The method of claim 1, wherein the matrix layer has a solubility for (−)-5,6,7,8-tetrahydro-6-[propyl-[2-(2-thienyl)ethyl]amino]-1-naphthalenol free base of ≥5% (w/w).

10. The method of claim 1, wherein (−)-5,6,7,8-tetrahydro-6-[propyl-[2-(2-thienyl)ethyl]amino]-1-naphthalenol free base is contained in the matrix in a concentration of from 5% to 25% (w/w).

11. The method of claim 1, wherein the soluble polyvinylpyrrolidone is admixed to provide a concentration of 1.5-5% (w/w) soluble polyvinylpyrrolidone in the matrix layer.

12. The method of claim 1, wherein the organic solvent comprises ethanol.

13. The method of claim 4, wherein following reaction of (−)-5,6,7,8-tetrahydro-6-[propyl-[2-(2-thienyl)ethyl]amino]-1-naphthalenol hydrochloride with the alkaline substance, the resulting adhesive solution containing (−)-5,6,7,8-tetrahydro-6-[propyl-[2-(2-thienyl)ethyl]amino]-1-naphthalenol free base is filtered to remove at least one by-product.

14. The method of claim 1, wherein the resulting matrix layer is a non-aqueous matrix layer.

15. The method of claim 1, wherein the matrix layer is a single-phase matrix.

16. The method of claim 11, wherein the soluble polyvinylpyrrolidone is admixed in an amount to provide a concentration of 1.5-3% (w/w) soluble polyvinylpyrrolidone in the matrix layer.

17. The method of claim 1, further comprising preparing a plaster having an area of 2 to 40 cm$^2$ from the matrix layer, said plaster containing 1 to 10 mg of the (−)-5,6,7,8-tetrahydro-6-[propyl-1[2-(2-thienyl)ethyl]amino]-1-naphthalenol free base.

18. The method of claim 17, wherein the plaster has an area of approximately 20 cm$^2$.

19. The method of claim 1, wherein a backing layer is applied to the matrix layer on the side thereof opposing said sheet, and wherein said sheet forms a removable protective layer.

* * * * *